(12) United States Patent
Berry et al.

(10) Patent No.: US 7,879,986 B2
(45) Date of Patent: Feb. 1, 2011

(54) DARK QUENCHERS, PROBES AND OTHER CONJUGATES INCORPORATING THE SAME, AND THEIR USE

(75) Inventors: David A. Berry, Ann Arbor, MI (US); William H. Pearson, Ann Arbor, MI (US)

(73) Assignee: Berry & Associates, Inc., Dexter, MI (US)

( * ) Notice: Subject to any disclaimer, the term of this patent is extended or adjusted under 35 U.S.C. 154(b) by 1119 days.

(21) Appl. No.: 11/346,688

(22) Filed: Feb. 3, 2006

(65) Prior Publication Data

US 2006/0177857 A1 Aug. 10, 2006

Related U.S. Application Data

(60) Provisional application No. 60/650,643, filed on Feb. 4, 2005.

(51) Int. Cl.
*C09B 31/153* (2006.01)
*C07H 19/04* (2006.01)
*C12Q 1/68* (2006.01)

(52) U.S. Cl. ............................ 534/752; 534/727; 435/6

(58) Field of Classification Search ....................... None
See application file for complete search history.

(56) References Cited

U.S. PATENT DOCUMENTS

| | | | | |
|---|---|---|---|---|
| 4,359,398 | A * | 11/1982 | Cole et al. ............... | 252/299.1 |
| 6,007,992 | A | 12/1999 | Lin et al. | |
| 6,670,085 | B2 | 12/2003 | Jurban et al. | |
| 7,019,129 | B1 | 3/2006 | Cook | |
| 7,109,312 | B2 | 9/2006 | Cook | |
| 7,160,996 | B1 | 1/2007 | Cook | |
| 2002/0155484 | A1 | 10/2002 | Reed et al. | |
| 2003/0082547 | A1 | 5/2003 | Ewing et al. | |
| 2003/0096254 | A1 | 5/2003 | Reed et al. | |
| 2003/0215728 | A1 | 11/2003 | Jurban et al. | |

FOREIGN PATENT DOCUMENTS

JP 4-361088 * 12/1992

OTHER PUBLICATIONS

Behlke, Mark, et al., Fluorescence and Fluorescence Applications, Integrated DNA Technologies, 2005, pp. 1-13.
Wojczewski, C., et al., Fluorescent oligonucleotides—versatile tools as probes and primers for DNA and RNA analysis, Synlett 1999, No. 10, pp. 1667-1678.
Miyawaki, A., et al., Lighting up cells: labelling proteins with fluorophores, Imaging in Cell Biology, Sep. 2003, 5, pp. S1-S7.
Tyagi, S., et al., Wavelength-shifting molecular beacons, Nature Biotechnology, vol. 18, Nov. 2000, pp. 1191-1196.
Walter, N. G., et al., Fluorescence assays to study structure, dynamics, and function of RNA and RNA-ligand complexes, Methods in Enzymology, 2000, vol. 317, pp. 409-440.
Heid, C. A., et al., Real time quantitative PCR, Genome Research, 1996, pp. 986-994.
Marras, S.A.E., et al., Efficiencies of fluorescence resonance energy transfer and contact-mediated quenching in oligonucleotide probes, Nucleic Acids Res., 2002, vol. 30, No. 21, pp. 1-8.
Tyagi, S., et al., Molecular beacons: Probes that fluoresce upon hybridization, Nature Biotechnol, vol. 14, Mar. 1996, pp. 303-308.
Morley, John, et al., Calculations of the electronic Spectra and Hyperpolarisabilities of Selected Dyes and Pigments, J. Chem. Soc. Faraday Trans., 1991, pp. 3021-3025.
Waggoner, A., Covalent labeling of proteins and nucleic acids with fluorophores, Methods in Enzymology, 1995, vol. 246, pp. 362-377.
Hua, Jianli, et al., Arylaldehydes-pentafluorophenyl Hydrazones as Second-order Nonlinear Optical Chromophores: A Novel Approach for Remarkably Defeating the Nonlinearity-transparency Trade-Off, Chemistry Letters 2002, pp. 232-233.
Hartmann, H., et al., On the coupling of aryldiazonium salts with N,N-disubstituted 2-aminothiophenes and some of their carbocyclic and heterocyclic analogues, J. Chem. Soc., Perkin Trans. 1, 2000, pp. 4316-4320.
Hutchings, M., et al., The Comparative Solvatochromism of Arylazo and Heteroarylazo Compounds Based on N,N-Diethyl-m-acetylaminoaniline and N,N-Diethyl-m-toluidine, Chem. Eur. J., 1997, 3, No. 10, pp. 1719-1727.
Beaucage, S.L., et al., Synthetic Strategies and Parameters Involved in the Synthesis of Oligodeoxyribonucleotides According to the Phosphoramidite Method, Current Protocols in Nucleic Acid Chemistry (2000) pp. 3.3.1-3.3.20.
Sharkey, F. Banat, et al., Detection and Quantification of Gene Expression in Environmental Bacteriology, Applied and Environmental Microbiology, Jul. 2004, vol. 70, No. 7, pp. 3795-3806.
Yuguan, S., et al., The synthesis of highly active thiophene ring-containing chromophore components for photonic polymers based on a newly designed route, J. Chem. Soc., Perkin Trans. 1, 1999, pp. 3691-3695.

(Continued)

*Primary Examiner*—Fiona T Powers
(74) *Attorney, Agent, or Firm*—Young, Basile, Hanion, & MacFariane, P.C.

(57) ABSTRACT

The specification discloses quenchers of excited state energy, probes and other conjugates comprising the same, and methods for their use. The quenchers of excited state energy have a structure comprising at least one reactive functional group for linking the quencher to a carrier molecule and at least three radicals covalently linked via exocyclic diazo bonds, the at least three radicals including at least one comprising a julolidine of the nominal formula:

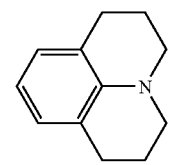

and the remainder of the at least three radicals being selected from the group of substituted and unsubstituted aryls, substituted and unsubstituted heteroaryls, and combinations thereof.

22 Claims, 6 Drawing Sheets

OTHER PUBLICATIONS

Jones, F., et al., Order Parameters of Dyes in a Biphenyl/Terphenyl Liquid Crystal Mixture, Mol. Cryst. Liq. Cryst., 1980, vol. 60, pp. 99-110.

Kim, Jae J., et al., Synthesis, structure, and UV-VIS absorption spectra of azo dyes derived from (dialkylamino)thiazole dimers, J. Cehm. Soc. Perkin Trans. 2, 2001, pp. 379-387.

Marras, S.A.E., et al., Multiplex detection of single-nucleotide variations using molecular beacons, Genetic Analysis: Biomolecular Engineering, 14 (1999) pp. 151-156.

Thiesen, P., et al., Fluorescent Dye Phosphoramidite Labelling of Oligonucleotides, Tetrahedron Letters, vol. 33, No. 35, 1992, pp. 5033-5036.

Ellington, A., et al., Introduction to the Synthesis and Purification of Oligonucleotides, Current Protocols in Nucleic Acid Chemistry (2000), pp. A.3C.1-A.3C.22.

Advances in RNA Synthesis and Structural Analysis, vol. 11, No. 2, Dec. 1998, pp. 1-12.

Invitrogen. Technical Focus: Fluorescence Resonance Energy Transfer [online]. Original publication date unknown. Retrieved [Feb. 4, 2008] Retrieved from the Internet: http://www.probes.com/handbook/boxes/0422.html.

Molecular Probes. Introduction to Amine Modification[online]. Original publication date unknown. Retrieved Feb. 4, 2008 from the Internet: http://www.probes.com/handbook/print/0101.html.

Molecular Probes. Detecting Nucleic Acid Hybridization [online]. Original publication date unknown. Retrieved Feb. 4, 2008 from the Internet: http://www.probes.com/handbook/print/0805.html.

Molecular Probes. Introduction to Thiol Modification and Detection [online]. Original publication date unknown. Retrieved Feb. 4, 2008 from the Internet: http://www.probes.com/handbook/print/0201.html.

Molecular Probes. Introduction to fluorescence Techniques [online]. Original publication date unknown. Retrieved Feb. 4, 2008 from the Internet: http://www.probes.com/handbook/print/0001.html.

* cited by examiner

BHQ-1

BHQ-2

BHQ-3

FIG. 4 Prior Art

Specific example:

Specific examples:

Specific example:

DMT = 4,4'-dimethoxytrityl
Icaa = long-chain aminoalkyl
CPG = controlled-pore glass

FIG. 7

Specific example:

DMT = 4,4'-dimethoxytrityl

DARK QUENCHERS, PROBES AND OTHER CONJUGATES INCORPORATING THE SAME, AND THEIR USE

CROSS-REFERENCE TO RELATED APPLICATIONS

This application is related to, and claims the benefit of priority from, U.S. Provisional Patent Application Ser. No. 60/650,643, filed Feb. 4, 2005.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

FIELD OF THE INVENTION

The present invention pertains to the field of so-called "dark quenchers" for donor-acceptor energy transfers, such as are employed, for instance, in fluorescent probes, as well as other conjugates comprising such quenchers, and methods of their use. The present invention more particularly pertains to such quenchers comprising at least one reactive functional group for linking the quencher to a carrier molecule and at least three radicals covalently linked via exocyclic diazo bonds, the at least three radicals including at least one comprising a julolidine with the remaining radicals being selected from the group consisting of substituted and unsubstituted aryls, substituted and unsubstituted heteroaryls, and combinations thereof.

BACKGROUND

In modern scientific research, the employment of fluorescent probes has become nearly indispensable as an analytical tool for detecting and quantifying molecular species, including, for example, chemical/biochemical substances.

Figure 1:
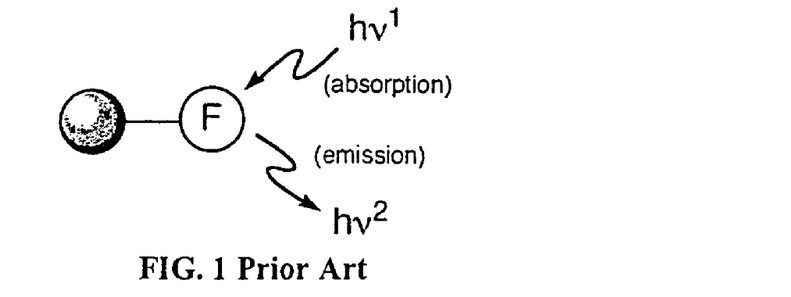
FIG. 1 is a schematic representation of a first category of prior art fluorescent probes.

Such fluorescent probes comprise, in their most basic form, molecules known as fluorophores which, upon the absorption of light, re-radiate this energy as a photon of light that is easily distinguished from scattered excitation light. This process is shown in FIG. 1, schematically representing just such a simple fluorophore (F) compounded with a target molecule (T). As depicted, the fluorophore, upon excitation by absorption of a photon of energy $hv^1$, for instance from a laser, light-emitting diode, etc., is detectable by observing the emission of a fluorescent photon at a lower energy $hv^2$ (the wavelength of the emitted electron is always longer due to loss of some energy in the excited state by reason of molecular motion—e.g., heat). The utility of this most basic structure is limited, however, including the fact that fluorescence is not specific to bound probes.

Figure 2:
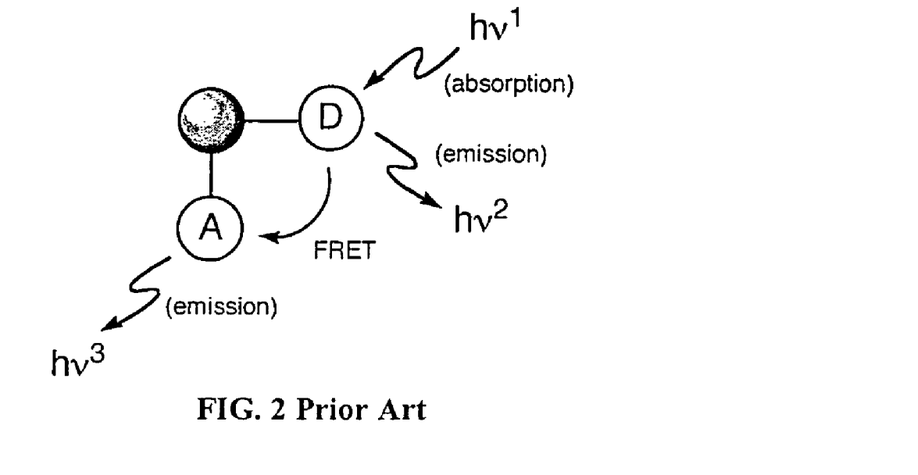
FIG. 2 is a schematic representation of a second category of prior art fluorescent probes.

According to a variant form, shown in FIG. 2, commonly referred to as a dual-labeled FRET ("Förster Resonance Energy Transfer") probe, there is provided a donor fluorophore (D) which functions to absorb a photon at energy $hv^1$ to produce an excited state donor that, in turn, may emit a photon $hv^2$ as in the previous example. However, the presence of an acceptor fluorophore (A) may, by reason of direct dipole-dipole interactions between the two fluorophores (A and D), result in transfer of the excited state energy from the donor (D) to the acceptor (A) without photon emission. This process results in the quenching of the donor (D) and the formation of an excited state acceptor (A) which may, in turn, emit a photon of a different (longer) wavelength, $hv^3$. The efficiency of this energy transfer depends upon the extent of overlap between the two fluorophores' emission spectra and the relative orientation of their transition dipoles.

Probes utilizing the foregoing structure are capable of a self-quenching functionality. For instance, FRET probes have been developed for nucleic acid hybridization assays wherein the probe hybridizes to itself in the absence of a target molecular species so that the donor and acceptor are in close proximity, thus quenching photon emission. In the presence of the target molecular species, by contrast, the probe preferentially hybridizes this structure to yield an increase in the physical distance between the donor and acceptor to thus permit photon emission and, accordingly, detection of the bound target molecular species.

FRET probes such as described, while conventionally in wide use, suffer from a number of drawbacks including, notably, fluorescent emission from the quencher compound which produces an undesirable background fluorescence.

Figure 3:
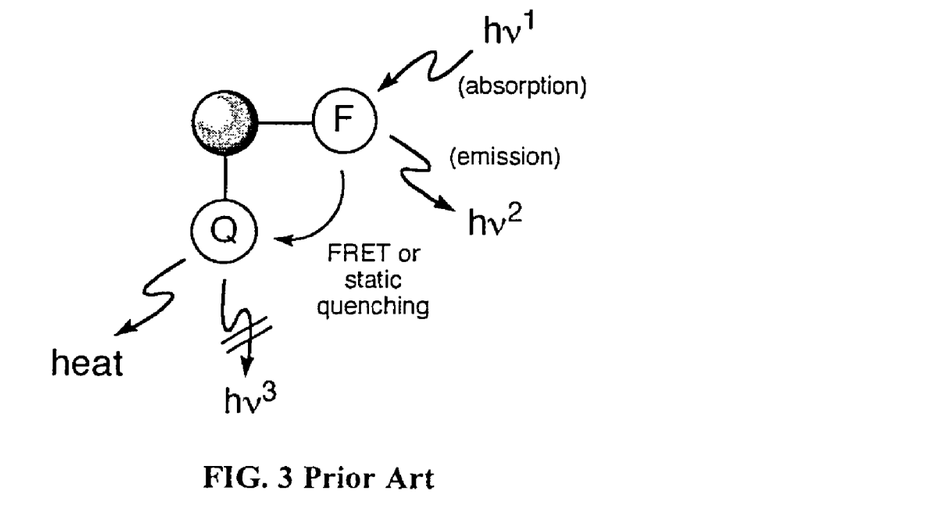
FIG. 3 is a schematic representation of a third category of prior art fluorescent probes.

In an effort to overcome the drawbacks attending both prior art probe variants described above, a third variant form, shown in FIG. 3, has been developed which comprises a fluorophore (F) and a so-called "dark-quencher" (Q). Dark-quenchers may be distinguished from the acceptor fluorophore (A) of FIG. 2 by their characteristic absorption of energy from a light source or another molecule without subsequent emission of a fluorescence photon (the excited state of the dark-quencher returns to the ground state by non-fluorescent decay—e.g., heat). Apart from this distinguishing characteristic, the principle of operation of dark quenchers is quite similar to that of the FRET probes described previously in that, depending upon the distance between the fluorophore (F) and the quencher (Q), the quenching interaction—that is, the absorption of energy by the quencher—may be accomplished through FRET, described above, or via static quenching. And by selectively distancing the fluorophore (F) and quencher (Q), desired fluorescence signaling is triggered. More particularly, when the fluorophore (F) and quencher (Q) are in close proximity (the "quenched state"), a photon $hv^1$ may be absorbed but emission of a photon $hv^2$ cannot occur due to FRET or static quenching. However, at longer distances of separation, such as may be occasioned by a binding or enzymatic cleavage event resulting in the relative separation of the quencher (Q) and fluorophore (F), consequent emission of a fluorescent signal ($hv^2$) is enabled.

Many modifications of the fundamental dark quencher structure described above have been developed. For example, there is provided in the disclosure of Cook et al., International Publication No. WO01/86001 A1, assigned to Biosearch Technologies, Inc., the disclosure of which is incorporated herein by reference in its entirety, dark-quenchers of the exemplary structures of FIG. 4, each of which is characterized by an aromatic donor comprising a N,N-dialkylaniline. Probes comprising such quenchers are advantageous in their characteristic long-wavelength (disclosed to be preferably from about 500 nm to about 700 nm) absorption maxima. However, this particular modification of the dark quencher variant is, in the longest (approximately 673 nm) wavelength quenching version (designated "BHQ-3" in FIG. 4) thereof, characterized by a N-phenylphenazinium moiety which may be susceptible to nucleophilic attack, such as during oligonucleotide deprotection with ammonia and similar reagents, and so creates stability problems when the quencher is conjugated with at least certain carrier molecules comprising the probe.

Accordingly, there continues to exist a need for dark-quenchers, and probes comprising the same, which are at once capable of long-wavelength absorption maxima to accommodate the growing trend towards fluorophores with longer wavelength emission spectra, as well as being characterized by greater stability than that achievable with conventional dark quenchers such as described.

SUMMARY OF THE INVENTION

The specification describes quenchers of excited state energy, probes and other conjugates incorporating the same, and methods of their use, such quenchers having a structure comprising a quencher of excited state energy having a structure comprising at least one reactive functional group for linking said quencher to a carrier molecule, and at least three radicals covalently linked via exocyclic diazo bonds, said at least three radicals including at least one comprising a julolidine of the nominal formula:

and the remainder of said at least three radicals being selected from the group consisting of substituted and unsubstituted aryls, substituted and unsubstituted heteroaryls, and combinations thereof.

In a first embodiment thereof, the inventive quenchers include those selected from the group of compounds characterized by the nominal formula:

and; wherein $Ar^1$ and $Ar^2$ are independently selected from the group consisting of substituted and unsubstituted aryls, and substituted and unsubstituted heteroaryls; X is selected from the group of O, S, and NR, where R is one of H, a C1 to C12 alkyl, a C3 to C10 cycloalkyl, or a C6 to C14 aryl; and Y comprises the at least one reactive functional group for linking the quencher to a carrier molecule, Y being associated with X via a linker.

According to one form of the foregoing, the aryl groups $Ar^1$ and $Ar^2$ are each independently selected from the group consisting of substituted and unsubstituted C6 to C14 aryls, and substituted and unsubstituted C6 to C14 heteroaryls.

Per yet another form of the compounds of the foregoing embodiment, the substituted aryls and substituted heteroaryls comprise one or more substituent's independently selected from the group consisting of electron-withdrawing groups and electron-donating groups. Exemplary electron-withdrawing groups include those selected from the group consisting of $NO_2$, CN, $CF_3$, $CO_2H$, $CO_2R$, $C(O)NH_2$, $C(O)NHR$, —$C(O)NR_2$, CHO, $C(O)R$, $SO_2R$, $SO_2NHR$, $SO_2NR^1R^2$, $SO_3H$, and $SO_3R$, wherein R is one of H, a C1 to C12 alkyl, a C3 to C10 cycloalkyl, and a C6 to C14 aryl, and $R^1$ and $R^2$ are each the same or different C1 to C12 alkyl, C3 to C10 cycloalkyl, or C6 to C14 aryl. Exemplary electron-donating groups comprise those selected from the group consisting of O(—), S(—), $NR^2$, NHR, $NH_2$, NHC(O)R, OR, OH, OC(O)R, SR, SH, Br, I, Cl, R, and C6 to C14 aryls, wherein R is one of a C1 to C12 alkyl, a C3 to C10 cycloalkyl, or a C6 to C14 aryl.

In one form of the foregoing embodiment, $Ar^1$ is a 4-nitrophenyl group, and $Ar^2$ comprises a phenyl ring attached to the two diazo groups in a 1,4 relationship, the phenyl ring bearing $OCH_3$ groups at positions 2 and 5.

Exemplary compounds according to the present invention include those selected from the group characterized by the nominal formula:

and; wherein W is H or $SO_3Na$, and Z comprises the linker.

According to another form of the inventive quencher compounds, the at least one reactive functional group comprises a sulfur-reactive electrophile. Exemplary compounds according to the foregoing include those selected from the group consisting of the following nominal compounds (I) and (II):

(I)

-continued (II)

and; wherein n is an integer from 1 to 5.

In still another form, the quenchers of the present invention further comprise a cleavable support for binding the quencher to a substrate, and the at least one reactive functional group comprises a hydroxyl group protected by a 4,4'-dimethoxytrityl (DMT) group or an analog thereof. Exemplary quenchers according to this form of the invention include those characterized by the following nominal formula:

and; wherein Z comprises the linker, and S comprises the cleavable support.

According to still another form of the inventive quenchers, the at least one reactive functional group comprises a protected phosphorous group. Exemplary quenchers according to this form include those selected from the group of compounds characterized by the nominal formula:

and; wherein $R^3$ and $R^4$ are the same or different alkyl groups, $R^5$ is methyl or $CH_2CH_2CN$, and Z is the linker. Still other exemplary compounds according to the foregoing include those selected from the group of compounds characterized by the nominal formula:

and; wherein n is an integer from 1 to 5.

In still another form of the inventive quenchers, the at least one reactive functional group comprises a protected phosphorous group and a hydroxyl group protected by a 4,4'-dimethoxytrityl (DMT) group or an analog thereof. A first exemplary compound according to this form is that characterized by the following formula:

According to a further form of the present inventive quenchers, the at least one reactive functional group comprises a nucleoside bearing a protected phosphorous group and a protected hydroxyl group, such as, for example, a hydroxyl group protected by a 4,4'-dimethoxytrityl (DMT) group or an analog thereof. Exemplary compounds according to the foregoing include those selected from the group of compounds characterized by the nominal formula:

and; wherein NB is a nucleobase, $R^3$ and $R^4$ are the same or different alkyl groups, and $R^5$ is methyl or $CH_2CH_2CN$, and Z is the linker. More particularly, exemplary compounds according to this form of the invention include those selected from the group of compounds characterized by the nominal formula:

and; wherein n is an integer from 1 to 5. More specifically still, an exemplary compound according to the foregoing form is that characterized by the following formula:

The present invention also comprehends conjugates of the foregoing quenchers and carrier molecules such as peptides, saccharides, nucleic acids, oligonucleotides, proteins, antibodies, and combinations thereof.

According to one embodiment, such conjugates comprise a fluorophore, with the fluorophore and the quencher constituting a donor-acceptor energy transfer pair.

The present disclosure further contemplates a methodology for detecting the presence of a molecular species in a given sample. In a first embodiment thereof, the inventive method comprises the steps of contacting a sample with at least one probe capable of interacting with the molecular species, the at least one probe comprising a carrier molecule bearing at least one fluorophore and at least one quencher according to the instant invention; and detecting the presence of the molecular species through a change in the fluorescence of the at least one probe.

In a second embodiment, the inventive method comprises the steps of contacting a sample with at least two probes capable of interacting with the molecular species, one of the at least two probes comprising at least one fluorophore, and the other of the at least two probes comprising a carrier molecule bearing at least one quencher according to the instant invention, and detecting the presence of the molecular species through a change in the fluorescence of the one of the at least two probes comprising at least one fluorophore.

According to either of the foregoing embodiments, the quenchers employed in the inventive methodologies may take the form of any of the compounds herein disclosed.

WRITTEN DESCRIPTION

Referring now to the written specification and the drawings, wherein like numerals indicate like or corresponding parts throughout the several views, the present invention will be seen to most generally comprise dark quenchers of excited state energy, probes and other conjugates comprising the same, and methods of their employment. More particularly, quenchers of the present invention have a structure comprising at least one reactive functional group for linking the quencher to a carrier molecule, and at least three radicals covalently linked via exocyclic diazo bonds, said at least three radicals including at least one comprising a julolidine of the nominal formula:

and the remainder of said at least three radicals being selected from the group consisting of substituted and unsubstituted aryls, substituted and unsubstituted heteroaryls, and combinations thereof.

Exemplary quenchers from those as more broadly described herein include those compounds selected from the group characterized by the following nominal formula:

wherein $Ar^1$ and $Ar^2$ are independently selected from the group consisting of substituted and unsubstituted aryls, and substituted and unsubstituted heteroaryls; X is selected from the group of O, S, and NR, where R is one of H, a C1 to C12 alkyl, a C3 to C10 cycloalkyl, or a C6 to C14 aryl; and Y comprises the at least one reactive functional group for linking the quencher to a carrier molecule, Y being associated with X via a linker.

The radicals $Ar^1$ and $Ar^2$ may each be independently selected from the group consisting of substituted and unsubstituted C6 to C14 aryls, and substituted and unsubstituted C6 to C14 heteroaryls. Exemplary aryls and heteroaryls include naphthyl, phenyl, and other all-carbon aromatic systems, and thiopene, thiazole, oxazole, and pyrazole. Where either or both $Ar^1$ and $Ar^2$ comprise substituted aryls and/or heteroaryls, the one or more substituents thereof may further be independently selected from the group consisting of electron-withdrawing groups and electron-donating groups. Exemplary electron-withdrawing groups include those selected from the group consisting of $NO_2$, CN, $CF_3$, $CO_2H$, $CO_2R$, $C(O)NH_2$, $C(O)NHR$, $C(O)_2$ CHO, $C(O)R$, $SO_2R$, $SO_2NHR$, $SO_2NR^1R^2$, $SO_3H$, and $SO_3R$, wherein R is one of H, a C1 to C12 alkyl, a C3 to C10 cycloalkyl, or a C6 to C14 aryls, and $R^1$ and $R^2$ are each independently selected from the group consisting of C1 to C12 alkyls, C3 to C10 cycloalkyls, and C6 to C14 aryls. Exemplary electron-donating groups include those selected from the group consisting of O(—), S(—), $NR^2$, NHR, $NH_2$, NHC(O)R, OR, OH, OC(O)R, SR, SH, Br, I, Cl, R, and C6 to C14 aryls, where R is one of a C1 to C12 alkyl, a C3 to C10 cycloalkyl, or a C6 to C14 aryl.

In the illustrated embodiments of the inventive quenchers, $Ar^1$ is shown to specifically constitute a 4-nitrophenyl group, while $Ar^2$ is a phenyl ring bearing $OCH_3$ groups at positions 2 and 5 and attached to the two diazo groups in a 1,4 relationship.

In the illustrated form of the present invention, X particularly comprises oxygen.

The functional group Y more particularly comprises one or more reactive functional groups for linking the quencher to a carrier molecule, such functional groups including, without limitation, sulfur-reactive electrophiles, protected nucleosides, and others as described in exemplary embodiments herein below.

Figure 4:
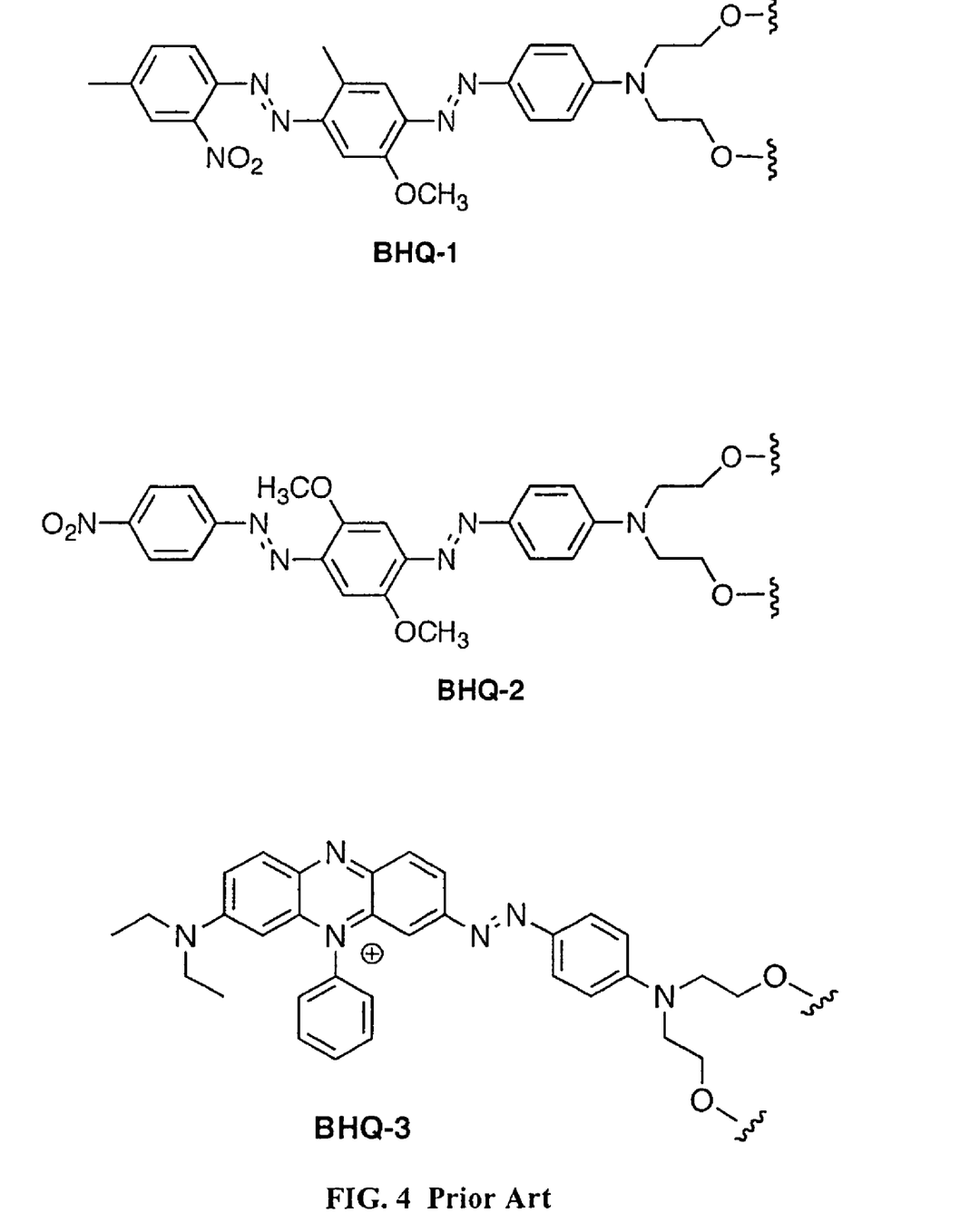
FIG. 4 illustrates the structural formula of several prior art quencher compounds from the disclosure of Cook et al., International Publication No. WO01/86001 A1.

The one or more functional groups are attached to the constituent X via a linker which may take any of numerous forms known to those skilled in the art, such as, without limitation, those shown in the illustrated embodiments of this invention, including beta-alkoxyethyl groups such as taught in the compounds of Cook et al., supra, and illustrated schematically in the compounds of FIG. 4, or a 1,2-diol, as depicted, also schematically, in the inventive quenchers shown in Table I, infra.

The quenchers of this invention are, as indicated, suited for attachment to a carrier molecule. As used herein, the term "carrier molecule" is intended to mean and refer broadly to any chemical or biochemical molecule to which attachment of the quenchers of this invention is desired, and may thus comprehend probes or compounds of other utility. By way of non-limiting example, carrier molecules suited to the present invention may be selected from among peptides, saccharides (including oligosaccharides, polysaccharides, etc.), nucleic acids, proteins, antibodies, oligonucleotides, etc. These and other such carrier molecules, means of making the same, and their manner of employment are well known to those of skill in the art.

In the attached, or conjugated, condition, the quencher/carrier molecule combination, or conjugate, is characterized by the following nominal formula:

Wherein M represents the carrier molecule linked to that portion of the quencher comprising the one or more functional groups, and Z represents the linker via which the one or more functional groups are associated with the rest of the quencher.

Non-limiting examples of nominal quenchers for attachment to specific carrier molecules, or components thereof, are shown below, and in more specific examples in FIGS. 5 through 9b. The manner of attaching such quenchers to a desired carrier molecule being known, the same will not be described further herein.

Figure 5:
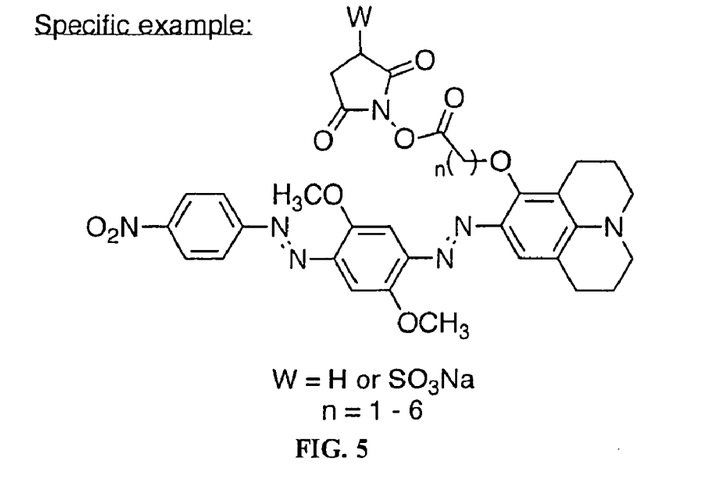
FIG. 5 is a first exemplary embodiment of a quencher compound according to the instant invention.

For attachment to the amino group of a carrier molecule, such as, for instance, an amine-modified oligonucleotide, there is provided, in one embodiment hereof, a group of quenchers of the following nominal formula:

wherein W is H or SO$_3$Na, and Z is the linker. Exemplary compounds based upon this nominal formula are shown in FIG. 5.

Figure 6A:
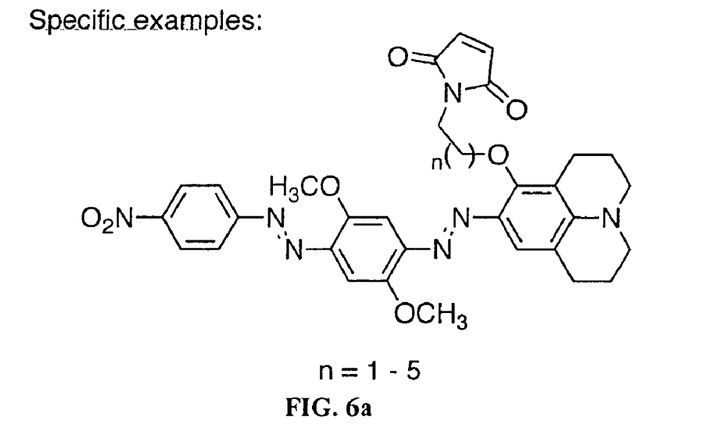
FIGS. 6a-6b show second and third exemplary embodiments of quencher compounds according to the instant invention.
Figure 6B:
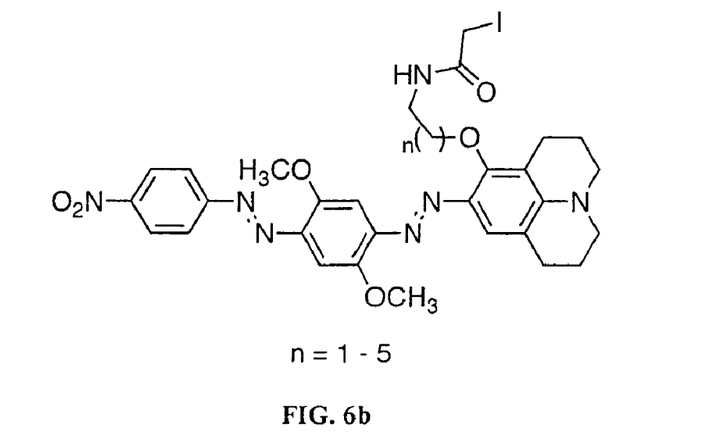

For attachment to the thiol group of a carrier molecule, such as, for instance, a thiol-bearing peptide or a thiol-modified oligonucleotide, there is provided, in another embodiment hereof, a group of quenchers of the following nominal formula:

wherein Q comprises a sulfur-reactive electrophile, and Z is the linker. Exemplary compounds based upon this nominal structure are shown in FIGS. 6a and 6b.

Figure 7:
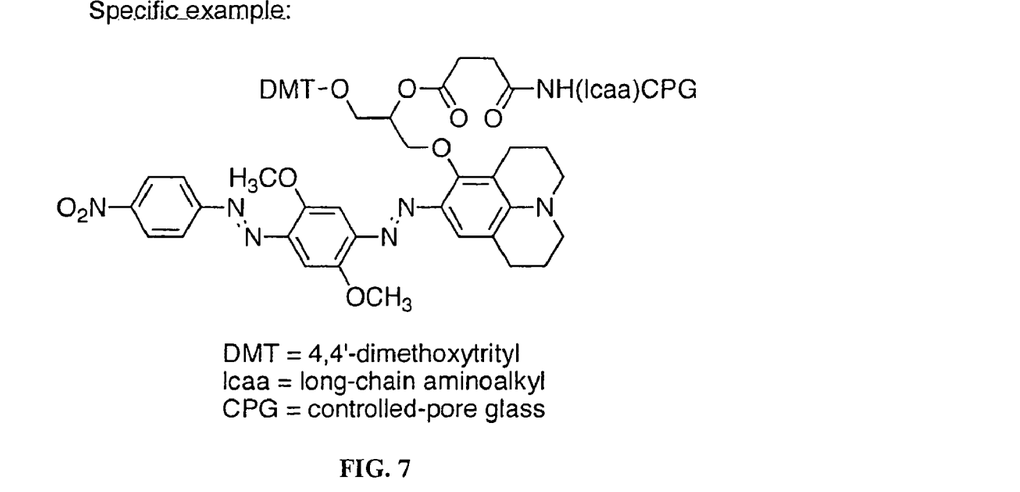
FIG. 7 is a fourth exemplary embodiment of a quencher compound according to the instant invention.

For installation at the 3'-terminus in oligonucleotide synthesis, there is provided, in yet another embodiment hereof, quencher compounds further comprising a cleavable solid support of conventional construction (e.g., controlled-pore glass, polystyrene bead, etc.) for binding the quencher to a substrate for oligonucleotide synthesis, and wherein the at least one reactive functional group comprises a hydroxyl group protected by a 4,4'-dimethoxytrityl (DMT) group or an analog thereof. Such compounds may be characterized by the following nominal formula:

wherein S represents the cleavable support, and Z represents the linker by which the support and the protected hydroxyl group are associated with the rest of the quencher. One exemplary compound based upon this nominal structure is shown in FIG. 7.

Figure 8A:
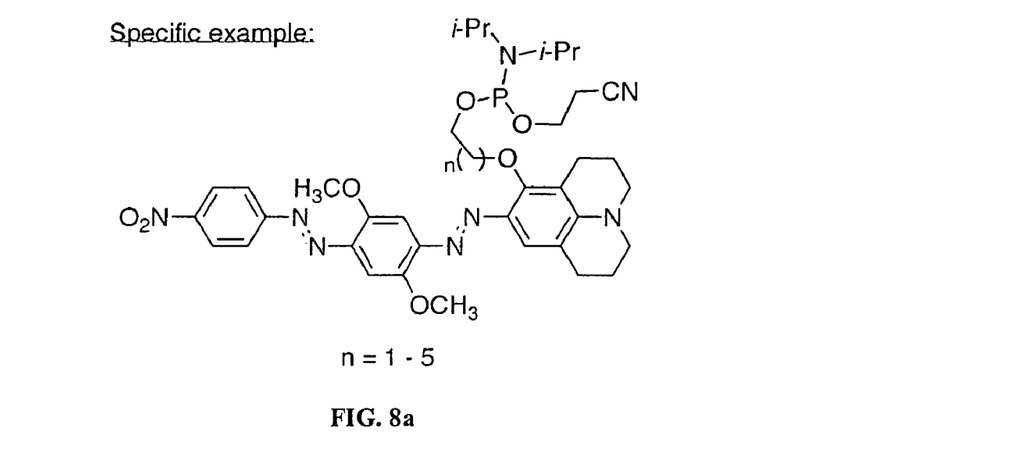
FIGS. 8a-8b show fifth and sixth exemplary embodiments of quencher compounds according to the instant invention.
Figure 8B:
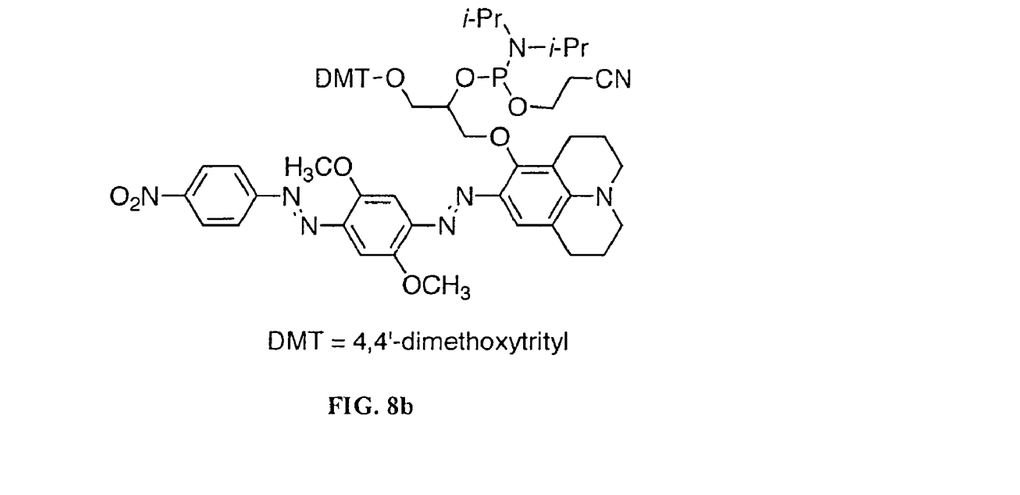

For attachment at the 5'-terminus of an oligonucleotide, there is provided, in another embodiment hereof, a group of quenchers having the following nominal formula:

wherein R$^3$ and R$^4$ are the same or different alkyl groups, R$^5$ is selected from the group of methyl and CH$_2$CH$_2$CN, and Z is the linker. Exemplary compounds based upon this nominal structure are shown in FIGS. 8a and 8b.

Figure 9A:
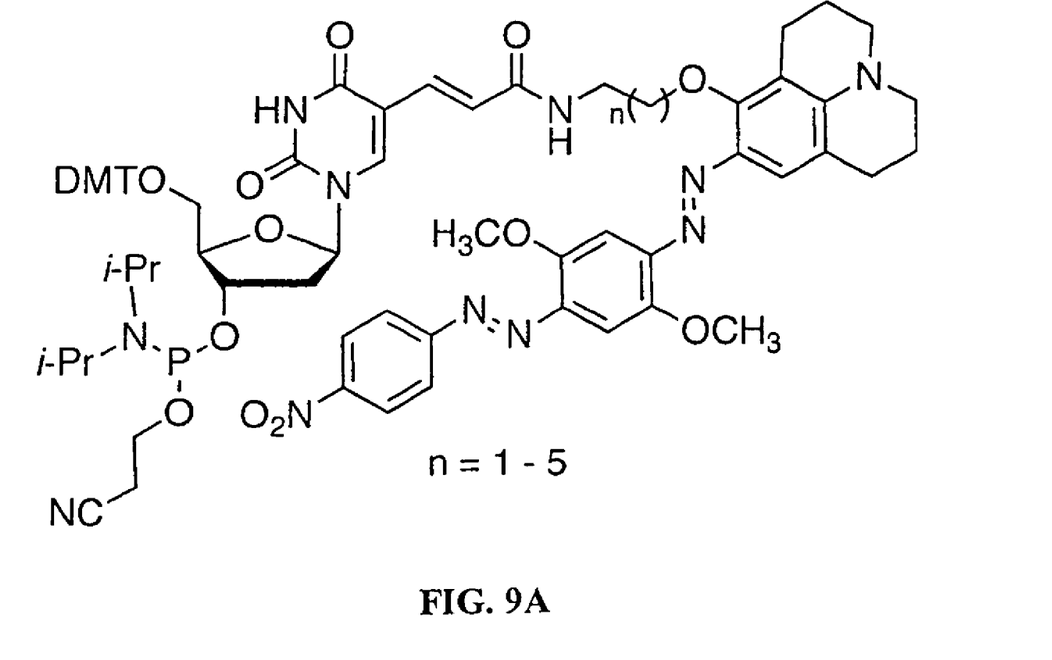
FIGS. 9a-9b depict seventh and eighth exemplary embodiments of quencher compounds according to the instant invention.
Figure 9B:
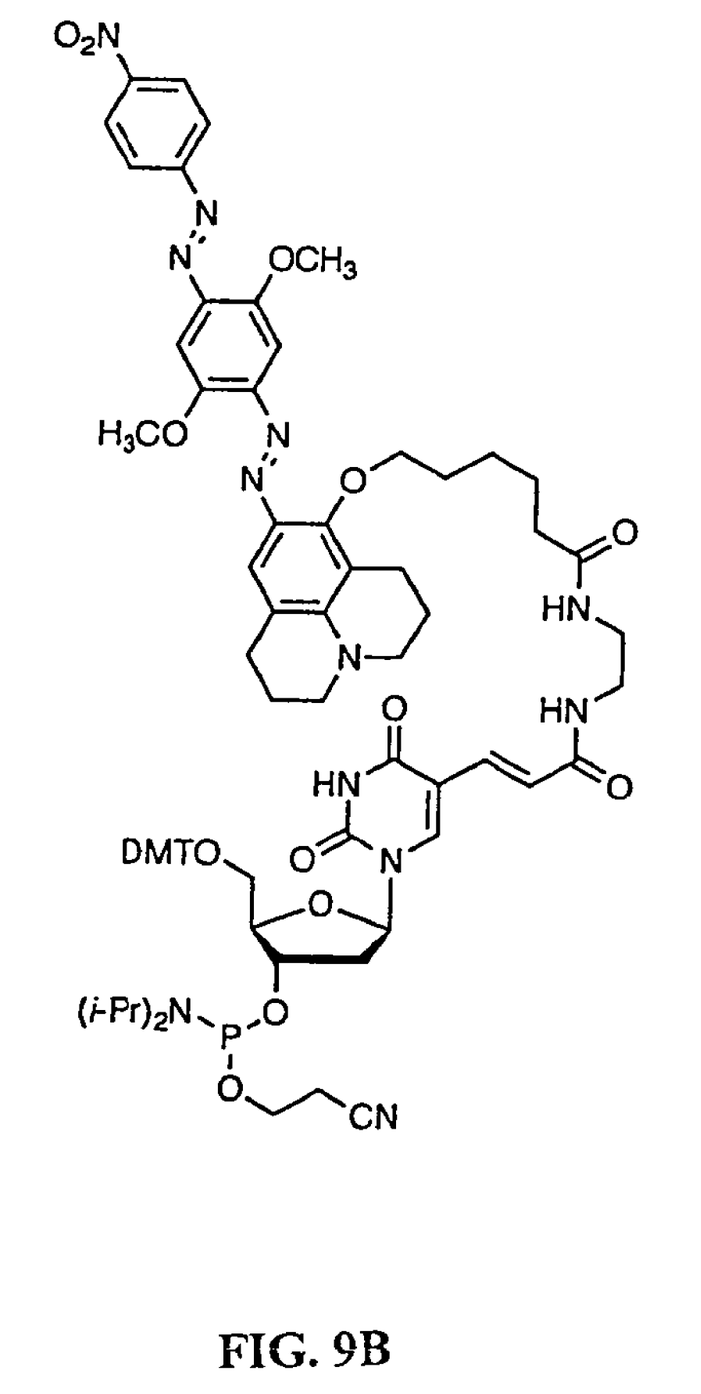

For installation in an internal position in an oligonucleotide, there is provided, in another embodiment hereof, a group of quenchers of the following nominal formula:

wherein NB is a nucleobase (i.e., adenine, guanine, uracil, cytosine, thymine, or analogs thereof), Z is the linker, R$^3$ and R$^4$ are the same or different alkyl groups, R$^5$ is selected from the group of methyl and CH$_2$CH$_2$CN, and DMT is 4,4'-dimethoxytrityl or an analog thereof. Exemplary compounds based upon this nominal structure are shown in FIGS. 9a and 9b.

As indicated, quenchers of the present invention, while capable of other utilities, are well-suited for use in probes employed in detecting the presence of a desired molecular species and especially well-suited for use in, or in conjunction with, fluorescent probes comprising at least one fluorophore, in which probes the fluorophore and quencher of this invention constitute a donor-acceptor energy transfer pair. Exemplary conventional fluorophores, the use and utility of which are well-known, are disclosed in Cook et al., WO 01/86001 A1, supra.

In use, fluorescent probes comprising the quenchers of this invention may be employed to detect the presence of a molecular species in a given sample. Such detection methodologies are well known in the art and, in combination with probes incorporating quenchers of the present invention, generally comprise the steps of: (1) contacting a sample with at least one probe capable of interacting with the molecular species, the at least one probe comprising one or both of at least one fluorophore and at least one quencher of excited state energy having a structure selected from among those described previously and (2) detecting the presence of the molecular species through a change in the fluorescence of the at least one probe.

According to another embodiment of this methodology, the at least one probe comprises both of the at least one fluorophore and the at least one quencher of excited state energy as specified previously. In another embodiment, at least two such probes are provided, each such probe comprising one or the other of the at least one fluorophore and the at least one quencher of this invention.

Though not depicted in Table I, further comparative study of the absorption maxima as between the same quencher according to the present invention and the compound designated BHQ-3 in the disclosure of Cook et al., supra (and shown in FIG. 4), both in oligonucleotide-conjugated form, show the inventive quencher to have an absorption maximum comparable to that of the BHQ-3 compound. And moreover, the inventive quencher demonstrates superior stability to the BHQ-3 compound and may thus be more easily incorporated into an oligonucleotide during solid-phase synthesis. For instance, testing has shown that cleavage and deprotection of oligonucleotides bearing the inventive quenchers with concentrated ammonium hydroxide and according to conventional protocols proceeds without significant degradation of these quenchers.

TABLE I

| Prior Art Quencher | $\lambda_{max}$ abs | |
|---|---|---|
|  BHQ-2 | 577 nm in oligo-nucleotide | |
| Inventive Quencher | $\lambda_{max}$ abs | $\Delta \lambda_{max}$ |
|  | 690 nm in oligo-nucleotide | +113 nm |

Referring now to Table I, below, there are provided data from a comparative study of the absorption maxima ($\lambda_{max}$ abs) for quencher/carrier conjugates comprising an exemplary quencher according to the present invention, and a prior art quencher from the disclosure of Cook et al., International Publication No. WO01/86001 A1, supra.

Referring particularly to the data in Table I, there is shown a comparison of the absorption maxima ("$\lambda_{max}$ abs") as between an exemplary quencher according to the present invention and the compound designated BHQ-2 in the disclosure of Cook et al. (and shown in FIG. 4), both conjugated with an oligonucleotide (only the unconjugated quencher is depicted). As shown, the inventive quencher shows a surprising and unexpected increase of 113 nm in its absorption maxima over the BHQ-2 compound of Cook et al., supra, in oligonucleotide-conjugated form.

It will be appreciated from the above disclosure that the present invention improves upon the prior art by providing quencher compounds which are at once characterized by long-wavelength absorption maxima and improved stability.

Of course, the foregoing is merely illustrative of the present invention, and those of ordinary skill in the art will appreciate that many additions and modifications to the present invention, as set out in this disclosure, are possible without departing from the spirit and broader aspects of this invention as defined in the appended claims.

The invention claimed is:

1. A quencher of excited energy state selected from the group of compounds having three radicals covalently linked via exocyclic diazo bonds, said three radicals including one that is a julolidine of the formula:

wherein a central radical is an unsubstituted aryl and wherein the radical positioned farthest from the julolidine is selected from the group consisting Of substituted and unsubstituted aryls, substituted and unsubstituted heteroaryls, and combinations thereof, and wherein at least one of the three radicals has at least one reactive functional group for linking said quencher to a carrier molecule.

2. quencher of excited energy state selected from the group of compounds of the following formula:

and; wherein $Ar^1$ and $Ar^2$ are independently selected from the group consisting of substituted and unsubstituted aryls, and substituted and unsubstituted heteroaryls;

X is selected from the group of O, S, and NR, where R is one of H a C1 to C12 alkyl, a C3 to C10 cycloalkyl, or a C6 to C14 aryl; and Y comprises the at least one reactive functional group for linking the quencher to a carrier molecule, Y being associated with X via a linker.

3. The quencher of claim 2, wherein $Ar^1$ and $Ar^2$ are each independently selected from the group consisting of substituted and unsubstituted C6 to C14 aryls, and substituted and unsubstituted C6 to C14 heteroaryls.

4. The quencher of claim 3, wherein the substituted aryls and substituted heteroaryls are substituted by one or more substituents independently selected from the group consisting of electron-withdrawing groups and electron-donating groups.

5. The quencher of claim 4, wherein:

(a) the electron withdrawing groups are selected from the group consisting of $NO_2$, CN, $CF_3$, $CO_2H$, $CO_2R$, C(O)$NH_2$, C(O)NHR, C(O)$NR_2$, CHO, C(O)R, $SO_2R$, $SO_2NHR$, $SO_2NR^1R^2$, $SO_3H$, and $SO_3R$, wherein R is one of H, a C1 to C12 alkyl, a C3 to C10 cycloalkyl, and C6 to C14 aryl, and $R^1$ and $R^2$ are each the same or different C1 to C12 alkyl, C3 to C10 cycloalkyl, or C6 to C14 aryl; and (b) the electron donating groups are selected from the group consisting of O(—), S(—), $NR^2$, NHR, $NH_2$, NHC(O)R, OR, OH, OC(O)R, SR, SH, Br, I, Cl, R, and C6 to C14 aryls, wherein R is one of a C1 to C12 alkyl, a C3 to C10 cycloalkyl, or a C6 to C14 aryl.

6. The quencher of claim 5, wherein $Ar^1$ is a 4-nitrophenyl group, and $Ar^2$ is a phenyl ring attached to the two diazo groups in a 1,4 relationship, the phenyl ring bearing $OCH_3$ groups at positions 2 and 5.

7. The quencher of claim 5, selected from the group of compounds of the formula:

wherein W is H or $SO_3Na$, and Z is the linker.

8. The quencher of claim 7, selected from the group of compounds of the formula:

wherein W is H or $SO_3Na$, and n is an integer from 1 to 6.

9. The quencher of claim 5, wherein the at least one reactive functional group comprises a sulfur-reactive electrophile.

10. The quencher of claim 9, selected from the group consisting of the following compounds (I) and (II):

(I)

(II)

wherein n is an integer front 1 to 5.

11. The quencher of claim 5, further comprising a cleavable support for binding the quencher to a substrate, and wherein the at least one reactive functional group is a hydroxyl group protected by a 4,4'- dimethoxytrityl (DMT) group.

12. The quencher of claim 11, wherein said quencher is of the following formula:

wherein Z is the linker, and S is the cleavable support.

13. The quencher of claim 5, wherein the at least one reactive functional group is a protected phosphorous group.

14. The quencher of claim 13, selected from the group of compounds of the formula:

wherein $R^3$ and $R^4$ are the same or different alkyl groups, $R^5$ is methyl or $CH_2CH_2CN$, and Z is the linker.

15. The quencher of claim 14, selected from the group of compounds of the formula:

wherein n is an integer from 1 to 5.

16. The quencher of claim 5, wherein the at least one reactive functional group is a protected phosphorous group and a hydroxyl group protected by a 4,4'-dimethoxytrityl (DMT) group.

17. The quencher of claim 16, of the following formula:

18. The quencher of claim 5, wherein the at least one reactive functional group is a nucleoside bearing a protected phosphorous group and a protected hydroxyl group.

19. The quencher of claim 18, wherein the at least one reactive functional group is a nucleoside bearing a protected phosphorous group and a hydroxyl group protected by a 4,4'-dimethoxytrityl (DMT) group.

20. The quencher of claim 19, selected from the group of compounds of the formula:

wherein NB is a nucleobase, $R^3$ and $R^4$ are the same or different alkyl groups, $R^5$ is methyl or $CH_2CH_2CN$, and Z is the linker.

21. The quencher of claim 20, selected from the group of compounds of the formula:

n = 1-5 wherein n is an integer from 1 to 5.

22. The quencher of claim 21, of the following formula:

UNITED STATES PATENT AND TRADEMARK OFFICE
CERTIFICATE OF CORRECTION

PATENT NO. : 7,879,986 B2
APPLICATION NO. : 11/346688
DATED : February 1, 2011
INVENTOR(S) : Berry et al.

Page 1 of 1

It is certified that error appears in the above-identified patent and that said Letters Patent is hereby corrected as shown below:

1. In Col. 3, line 67, please delete "substituent's" and insert --substituents--;

2. In Col. 15, line 10, please delete "unsubstituted aryl and wherein" and insert --unsubstituted aryl or a substituted aryl and wherein--;

3. In Col. 15, line 20, please delete "quencher" and insert --A quencher--; and

4. In Col. 15, line 40, please delete "H a" and insert --H, a--.

Signed and Sealed this
Fifth Day of April, 2011

David J. Kappos
*Director of the United States Patent and Trademark Office*